United States Patent [19]

Szody et al.

[11] Patent Number: 4,696,643
[45] Date of Patent: Sep. 29, 1987

[54] PROCESS AND APPARATUS FOR HEATING OF PASTY MATERIALS

[75] Inventors: Péter Szödy, Nagykata; Péter Dunajcsik, Budapest; Miklós Villányi, Budapest; Ferenc Bossánszky, Budapest; Endre Libor, Budapest; Ferenc Kiss, Budapest, all of Hungary

[73] Assignee: Budapest Muszaki Egyetem, Budapest, Hungary

[21] Appl. No.: 716,786

[22] Filed: Mar. 25, 1985

[30] Foreign Application Priority Data

Apr. 2, 1984 [HU] Hungary .............................. 1315/84

[51] Int. Cl.⁴ ................................................ F27B 9/00
[52] U.S. Cl. ................................. 432/120; 137/625.41
[58] Field of Search ...................... 432/95, 120; 34/25, 34/56, 168, 172, 173; 137/625.4, 625.41

[56] References Cited

U.S. PATENT DOCUMENTS 3,961,893  6/1976  Russell et al. ...................... 219/401
4,019,535  4/1977  Buckethal ...................... 137/625.41

*Primary Examiner*—Henry C. Yuen
*Attorney, Agent, or Firm*—Gabriel P. Katona

[57] ABSTRACT

Process and apparatus for the heating of pasty materials with surface and infusion type heating, wherein the two heating systems are combined in such a manner that first the pasty material is preheated by surface heating, then it is heated to the required final temperature by infusion heating due to the arrangement that the two heating systems are placed above each other. Also the preheated material is admitted into the infusion space lying below with a vertical velocity component and where it is elutriated in a field of gravity and drop formation takes place simultaneously with the preheating.

3 Claims, 5 Drawing Figures

PROCESS AND APPARATUS FOR HEATING OF PASTY MATERIALS

FIELD AND BACKGROUND OF THE INVENTION

The invention relates to a process and an apparatus for the heating of pasty materials by surface and infusion type heating.

The heating of pasty materials to high temperature is a frequent task in the industry (e.g. for the purpose of sterilization) by surface heat exchangers or apparatus used for direct heating.

A considerable part of the materials to be processed in the chemical-, pharmaceutical- and food-industry is heat-sensitive. Depending on the processed material, increase of the temperature is detrimental to the components of the material. The major part of the presently used apparatuses are heat exchangers, the various constructions of which may be suitable for the fast heating of the pumped products.

If the viscosity of the product to be processed is high, then from the viewpoint of the effective heat transfer and hydraulic resistance of the apparatus, only those of special construction may come into consideration. The highly viscous pasty materials in most cases contain solid components as well. The optimal processing of this kind of materials is not possible with the presently existing technical solutions.

The realization of the direct heating appears to be feasible for the fast heating of pasty materials. Such apparatuses are used for the heat treatment of liquescent materials in apparatuses functioning with injection or infusion system. The heating of pasty materials in such apparatuses raises serious technical problems.

In case of using infusion type apparatuses, the perfect mixing of the heating medium and the material is difficult to solve, due to the high viscosity.

When infusion type heaters are used where the product is atomized in the steam chamber, the high viscosity and the pressure of incidental solid components represent similar problems.

In case of using nozzles under pressure with one or two mediums, high differential pressure is required to bring about the atomization and the exit velocity of the liquid jet is also high. When drop aggregation with small characteristic size which is appropriate to the process is brought about, the differential pressure in the nozzle and the exit velocity exclude the use of infusion system, since it results in rather large dimensions of the apparatus.

Apart from the characteristic drop size obtained by atomization, the exit velocity influences the size of the heating chamber to a considerable extent. The direct heating takes place in the heating chamber where the heating medium is in direct contact with the drop emerging from the nozzle. The time of heat conduction required for the temperature determining the heat treatment is influenced, apart from the drop size, by the characteristics of the material. In order to provide adequate time for the heat conduction the drops should be in contact with the heating medium without agglutination of the drops. This reaction time determines the size of the heating chamber. In case of high exit velocity this may considerably increase the dimensions of the apparatus.

The diameter of the heating chamber is influenced by the size of the cone of dispersion emerging from the nozzle. In case of large cone of dispersion the diameter increses considerably which leads to the excessive increase of the wall thickness of the apparatus.

The use of disc atomizer in infusion type apparatus is not suitable either, since it similarly increases the diameter of the apparatus.

SUMMARY AND OBJECTS OF THE INVENTION

The purpose of the process and apparatus according to the invention is to eliminate the drawbacks appearing in the apparatuses operating with surface and direct heating owing to the high viscosity of the pasty materials and the realization of such solution which combines the advantages of both systems.

The principle of the invention is based on the recognition that a surface heat exchanger is to be arranged above the infusion space through which the heating medium and the material to be heated are admitted periodically alternately into the infusion space.

The object of the invention is the realization of an apparatus for the fast heating of pasty materials which combines the surface heat exchanger with the directly heating infusion type unit so that the drop entering the steam chamber passes into the infusion space in preheated condition with suitably small characteristic size and at low exit velocity.

This problem was solved by the combination of the two heating processes in such a way that first the pasty material is preheated by surface heating, then it is heated to the required final temperature by infusion heating so that the two heating processes are arranged above each other and, the preheated material is admitted into an infusion space with a vertical velocity component where it is elutriated in a field of gravity and the drop formation takes place simultaneously with the preheating.

The essence of the apparatus suitable for the realization of the process according to the invention is that the apparatus consists of a space of material, a steam chamber and an infusion chamber and a space divider is arranged between the three spaced provided with at least one through-hole and always two spaces only, namely the space of material and the infusion space or the steam chamber and the infusion space are interconnected through the holes.

The through-hole plays preferably at the same time the role of a forming element.

Suitably the space of material and the steam chamber are arranged above the infusion space and the space divider provided with the through-hole is arranged in between, furthermore the through-hole is always covered only by one space i.e. either by the space of material or the steam chamber, since the space of material and the steam chamber are arranged on a movable sliding surface.

According to another construction of the apparatus one of the material space and of the steam chamber is in constant contact via the through-hole in the space divider with the infusion space arranged underneath, while the other space, i.e. the space of material or the steam chamber is arranged in one of the spaces and connected via the through-hole in the space divider only periodically to the thid space, i.e. the infusion space. Preferably the infusion space is arranged excentrically and rotatably.

BRIEF DESCRIPTION OF THE DRAWINGS

The invention is described in detail with the aid of the drawings showing the construction of the apparatus shown by way of example only, in which.

DESCRIPTION OF THE PREFERRED EMBODIMENTS

Figure 1:
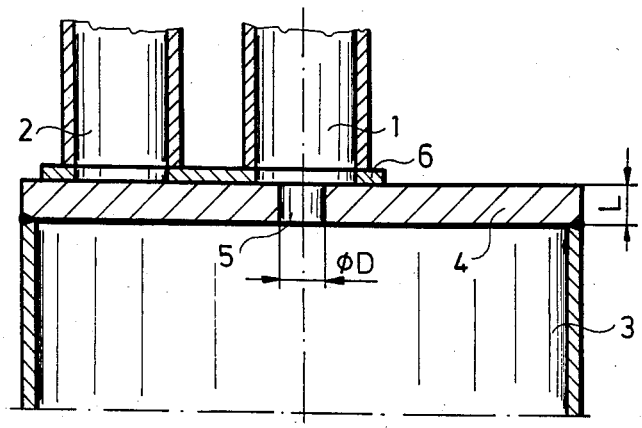
FIG. 1 is a schematic diagram of the apparatus.

The apparatus according to the invention consists of three spaces or chambers as shown in FIG. 1. The material to be heated is arranged in a space of material 1, the heating medium which is steam or gas of suitable pressure is in a steam chamber 2. An infusion space 3 is below the space of material 1 and steam chamber 2 with a space divider 4 in between. The space divider 4 is provided with a through-hole 5 of diameter D. The length of the through-hole 5 equals to the thickness L of the space divider 4. The space of material 1 and the steam chamber 2 are fixed into a sliding surface 6 movable to and fro above the space divider 4.

Figure 2:
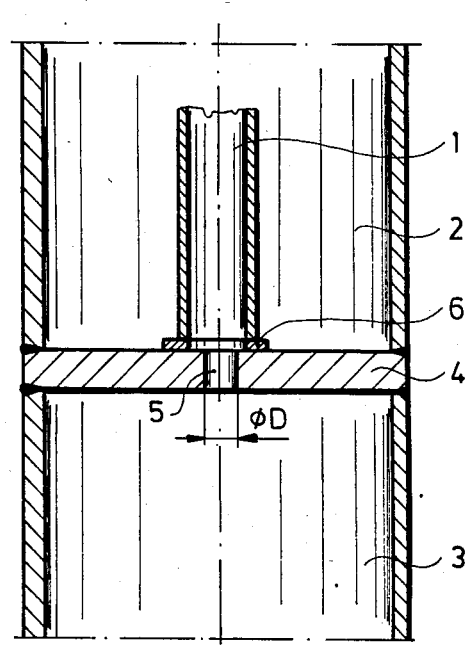
FIG. 2 is a schematic diagram of another embodiment.

The construction according to FIG. 2 differs from the one shown in FIG. 1 in that the space of material 1 is arranged concentrically inside the steam chamber 2 and the diameter of the infusion space 3 is the same as that of the steam chamber 2. The space divider 4 separating the steam chamber 2 and the infusion space 3 is provided suitably with a through-hole 5, the length of which equals to the thickness L of the space divider 4. The space of material 1 is arranged on a rotatable or sliding surface 6.

Figure 3:
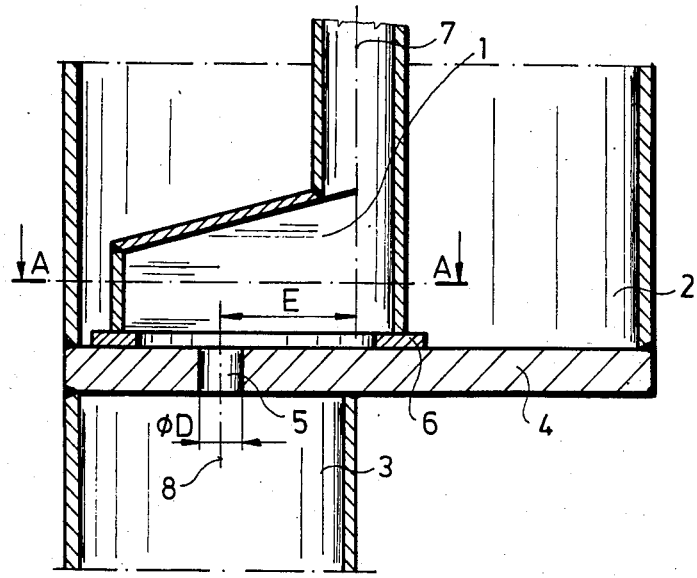
FIG. 3 is a schematic diagram of a further embodiment.
Figure 4:
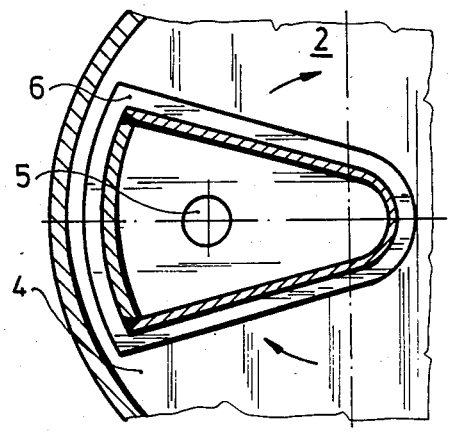
FIG. 4 is a section along line A—A shown in FIG. 3.

In the construction shown in FIG. 3 the space of material 1 is arranged similarly in the steam chamber 2, and the infusion space 3 is unerneath with the space divider 4 in between. It differs from the construction shown in FIG. 2 in that the centerlines 7, 8 of the space of material 1 and infusion space 3 do not coincide, but are displaced by distance E in relation to each other. The through-hole 6 in the space divider 4 is arranged in the centerline 8 of the infusion space 3, its length equals to the thickness L of the space divider 4. The space of material 1 is arranged excentrically and rotatably on the sliding surface 6. The sectional view of the excentric arrangement of the space of material 1 is shown in FIG. 4.

Figure 5:
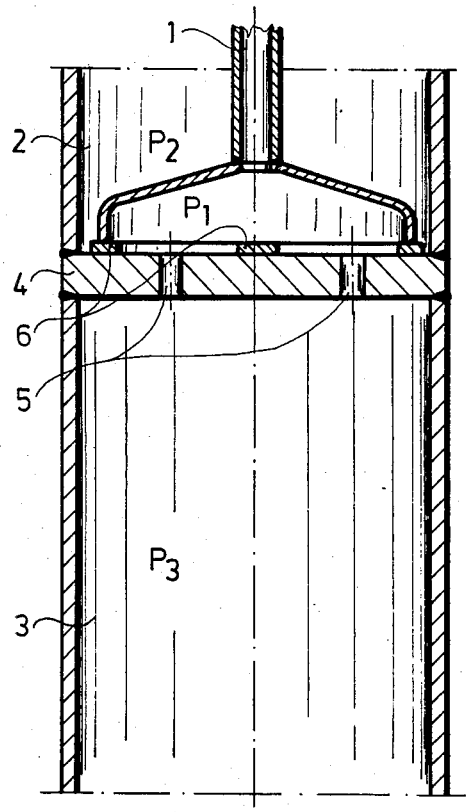
FIG. 5 is a schematic diagram of a further construction.

The construction shown in FIG. 5 is theoretically the same as the one shown in FIG. 2. Here also the space of material 1 is arranged in the steam chamber 2, while the infusion space 3 is arranged concentrically underneath. The difference is that several through-holes 5 are in the space divider 4 which can be opened or closed by turning the space of material 1 around the centerline 7.

The diameter D of the through-hole 5 depends on the viscosity of the material to be heated, and in case of clumpy materials, bone fragment or lumpy tomato or fruit pulp, on the size of the pieces.

The length of the infusion space 3 depends on the following:
 the final temperature required by the technology,
 the initial temperature of the material to be heated,
 the pressure of the heating medium,
 the diameter D of the through-hole,
 the characteristics of the material to be heated.

The apparatus according to the invention illustrated in the various figures functions as follows:

The material to be heated is admitted into the space of material 1 and the heating medium which is generally steam or gas under suitable pressure into the steam chamber 2. When the space of material 1 and the steam chamber 2 are jointly moved by the to and fro motion of the sliding surface 6, then the material flows through the through-hole 5 into the infusion space 3. If suitable differential pressure is available in the space of material 1 and the infusion space 3 then, depending on the characteristics of the material as well as on the diameter D and length L of the through-hole 5, a given quantity of material passes into the infusion space 3 where the drop emerging from the through-hole 5 falls down by gravitation. The velocity at which the drop falls by gravitation into the space of material 1 is the settling rate. The diameter D of the through-hole 5 is to be selected so that the drop should emerge from the through-hole 5 at a low rate in order to avoid the excessive length of the infusion space 3. If the space of material 1 and the steam chamber 2 are arranged alternately above the through-hole 5 by movement of the sliding surface 6, then the heating medium and the pasty material will flow alternately through the through-hole 5. By selection of a suitable cycle, the heating medium heats the mantle surface of the through-hole 5 in the space divider 4 and fills out the infusion space 3 so that on the one hand the through-hole 5 preheats the material flowing through and, on the other hand, for the heat conduction optimal temperature exists in the infusion space 3. The material to be heated, while it passes through the mantle surface of the through-hole 5, absorbs heat from the space divider 4, as a result of which it heats up to a given temperature and thus the preheated drop flows parallel with the centerline of the infusion space 3 at a low rate into the infusion space 3 where during its free-fall the direct heating takes place.

In the following cycle again the steam chamber 2 gets into contact with the infusion space 3 through the through-hole 5 and while the heating medium passes through the through-hole 5 its mantle surface transmits heat to the space divider 4 and the process is repeated periodically.

The material passes from the space of material 1 through the through-hole 5 into the infusion space 3 in each half-cycle. Meanwhile it dissipates heat from the space divider 4 through the mantle surface of the through-hole 5. In this manner the material is heated up to a given temperature then the preheated drop passes parallel with the centerline of the infusion space 3 at a low rate into the infusion space 3 where the direct heating takes place. In the second half-cycle the steam chamber 2 gets into contact with the infusion space 3 and while the heating medium passes through the through-hole 5 it transmits heat to the mantle surface of the hole to the space divider 4.

With the process and apparatus according to the invention local over-heating in the material to be heated is eliminated, an optimal size and velocity of the drop, as well as a velocity component of a specific direction are realized. The suitable preheating of the material is realized by the periodical heat transmission and heat dissipation of the space divider. This way the extent of the heat conduction phase of the infusion and the size of the apparatus can be considerably reduced without damaging the material.

What we claim is:

1. Apparatus for the heating of pasty materials with surface heating and infusion type heating, comprising a heating chamber for the material to be processed, a steam chamber, an infusion chamber, a space divider, said space divider being arranged between said chambers, a plurality of through holes, said through holes being formed in said space divider for selectively interconnecting at a time the infusion chamber with either the heating chamber or with the steam chamber, said space divider thereby acting as a heat exchanger between the said chambers, said heating chamber and said steam chamber being arranged vertically above the infusion chamber for enhancing the drop formation of the pasty material during the feeding thereof into said infusion chamber, said through holes communicating at one time only with one of said chambers, a sliding member for providing a connection between said heating chamber and said steam chamber, said heating and steam chambers being arranged on said sliding member, said heating and steam chambers being movable said space divider.

2. Apparatus as claimed in claim 1, characterized in that the through-holes are shaped for drop forming of said material.

3. Apparatus as claimed in claim 1 wherein said chamber of material is centrally located about a centerline of said apparatus and wherein said infusion chamber and said through-holes are arranged eccentrically in relation to the centerline said heating chamber being rotatable over said through-holes.

* * * * *

UNITED STATES PATENT AND TRADEMARK OFFICE
CERTIFICATE OF CORRECTION

PATENT NO. : 4,696,643
DATED : September 29, 1987
INVENTOR(S) : Peter Szdy et al.

It is certified that error appears in the above-identified patent and that said Letters Patent are hereby corrected as shown below:

Claim 1, in column 6, lines 1-2, change "at one time", to
--one at the time--;

line 6, change "movable said", to
--movable over said--.

Signed and Sealed this

Second Day of February, 1988

Attest:

DONALD J. QUIGG

Attesting Officer

Commissioner of Patents and Trademarks